United States Patent
Riccobono et al.

[11] Patent Number: 6,083,488
[45] Date of Patent: Jul. 4, 2000

[54] BARRIER TO PLAQUE FORMATION

[75] Inventors: Paul X Riccobono, Bedminster; Alfred J. Smetana, Wayne; Joseph Synodis, Summit, all of N.J.

[73] Assignee: The Block Drug Company, Jersey City, N.J.

[21] Appl. No.: 08/759,561

[22] Filed: Dec. 4, 1996

[51] Int. Cl.[7] .............................. A61K 9/46; A61K 7/16; A61K 31/74; A61K 31/75
[52] U.S. Cl. .................................................. 424/44; 424/49
[58] Field of Search ................................... 427/49–88, 44

[56] References Cited

U.S. PATENT DOCUMENTS

| | | | |
|---|---|---|---|
| 4,999,869 | 3/1991 | Holland et al. | 8/115.62 |
| 5,011,682 | 4/1991 | Elliott et al. | 424/52 |
| 5,013,541 | 5/1991 | Elliott et al. | 424/52 |
| 5,030,380 | 7/1991 | Moschner et al. | 252/186.2 |
| 5,055,217 | 10/1991 | Garcia et al. | 252/94 |
| 5,112,520 | 5/1992 | Krinski et al. | 252/174.23 |
| 5,266,166 | 11/1993 | Dreisbach et al. | 162/199 |
| 5,358,655 | 10/1994 | Kruse et al. | 252/95 |
| 5,518,645 | 5/1996 | Jean et al. | 252/108 |
| 5,531,915 | 7/1996 | Perkins | 510/294 |
| 5,534,183 | 7/1996 | Gopalkrishnan et al. | 510/434 |
| 5,536,440 | 7/1996 | Gopalkrishnan et al. | 510/417 |
| 5,565,145 | 10/1996 | Watson et al. | 510/350 |
| 5,576,282 | 11/1996 | Miracle et al. | 510/276 |
| 5,710,116 | 1/1998 | Miracle et al. | 510/276 |

FOREIGN PATENT DOCUMENTS

| | | |
|---|---|---|
| 358 472 | 3/1990 | European Pat. Off. . |
| 358 474 | 3/1990 | European Pat. Off. . |
| 358 473 | 3/1991 | European Pat. Off. . |

OTHER PUBLICATIONS

BASF Performance Chemicals Product Brochure Sokalan Specialty Polymers p. 11 HP22 1997.

*Primary Examiner*—Shep K. Rose
*Attorney, Agent, or Firm*—Craig M. Bell; Dann, Dorfman, Herrell and Skillman

[57] ABSTRACT

A denture cleansing agent containing a film forming material for preventing plaque formation. The denture cleansing agent may be a denture cleanser tablet, and the film forming material may be a polyoxyethylene oxide/vinyl acetate copolymer.

15 Claims, 1 Drawing Sheet

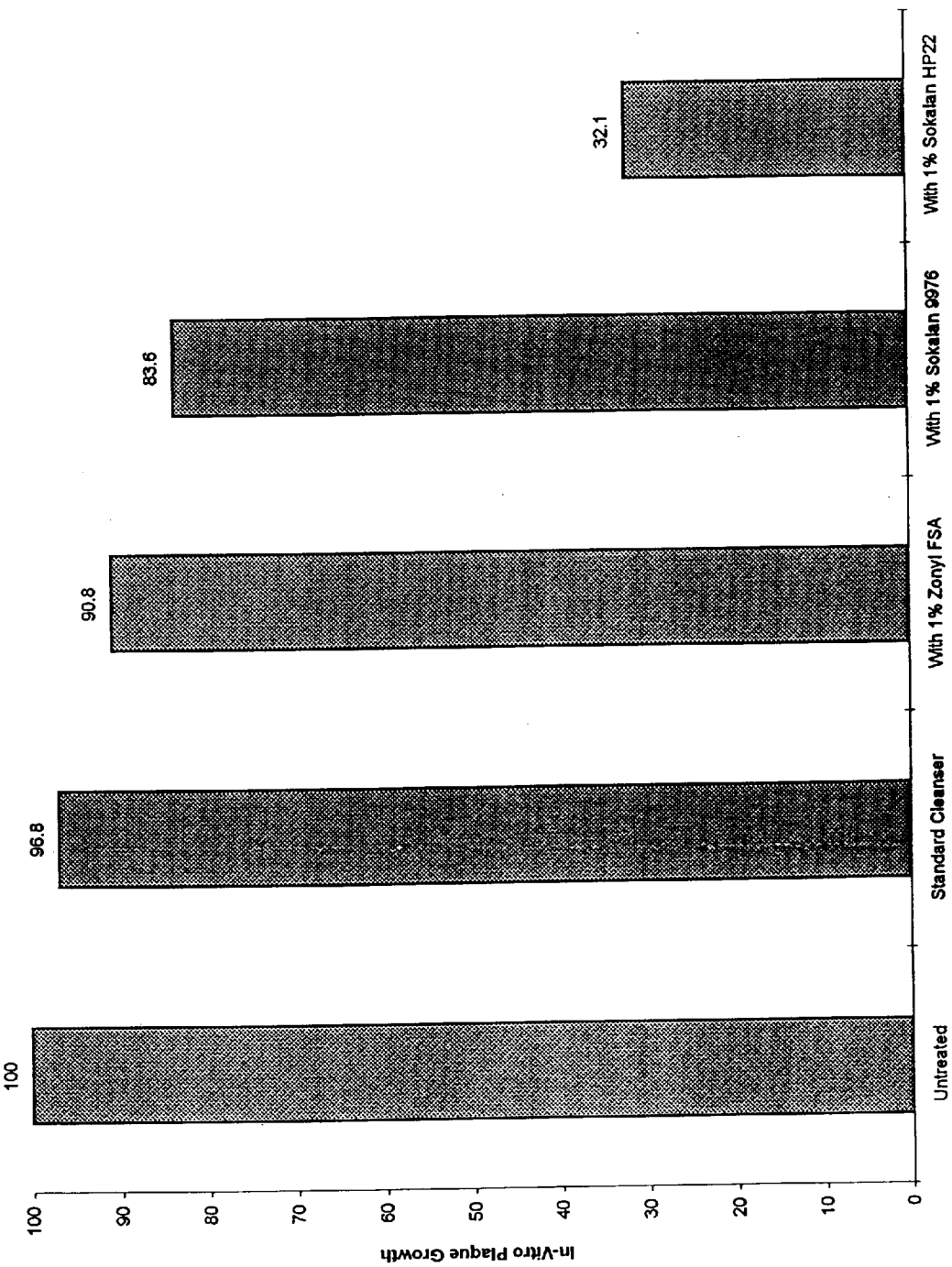

BARRIER TO PLAQUE FORMATION

FIELD OF THE INVENTION

This invention relates to compositions for the care and maintenance of good oral hygiene for users of full or partial dentures or other removable or permanent dental work such as bridges. The invention also relates to methods of making and using such compositions.

DESCRIPTION OF RELATED MATERIALS

It has long been recognized that the formation of dental plaque on teeth can lead to periodontal disease and tooth decay. What is often less recognized is that formation of plaque on full or partial dentures can also cause periodontal disease in gums. People with partial dentures or bridgework may experience tooth decay in remaining natural teeth as a result of plaque on the dental work.

Dental plaque results from cariogenic bacteria (e.g., Streptococcus mutans) that collect in colonies and form metabolic acids and deposits on tooth and denture surfaces. Plaque initiates when cariogenic bacteria adhere to the surface of dentures and teeth in the mouth. The metabolic acids produced by the bacteria degrade gum tissue and dental structure. Plaque deposition can lead to tartar buildup and other unsightly and unhealthful consequences.

Many approaches have been tried to prevent or treat plaque and associated calculus (tartar) on teeth, and some approaches have also been tried with dentures.

The most straightforward technique for reducing plaque is, of course, cleaning or brushing. With teeth, the most common forms of cleaning include brushing with a dentifrice and inundating the oral cavity with a mouth wash or mouth rinse. Dentures may also be brushed or soaked for some period outside the mouth for cleaning and removal of plaque. Depending on the method of attachment in the mouth, partial dental work may or may not be removed for cleaning. Partial dentures and bridgework, therefore, may either be brushed with natural teeth or cleaned separately, like dentures.

Unfortunately for both teeth and dentures, mechanical cleaning does not always reach all potential areas of plaque attachment. Spaces between teeth or dentures are not always cleaned with the necessary thoroughness. Mouth washes and mouth rinses are often not used for a fully sufficient time to accomplish the necessary cleaning. Denture cleansers are more effective at removing plaque than mouth rinses because they can be used for a longer period of time. Denture cleansers may also contain stronger cleaning ingredients, because the dentures are removed from the mouth before cleaning.

The difficulty inherent with all cleaning approaches is that the bacteria begin to regenerate and form plaque again as soon as cleaning has ended. Thus, cleaning only removes plaque once it has been deposited but can do nothing to prevent plaque from depositing in the first place. Even the strongest cleaning techniques necessarily leave the teeth and dentures exposed to plaque bacteria between cleanings.

Fluoride treatments have been used for some time to strengthen natural teeth against cariogenic attack, but such treatments do nothing to prevent the attack from occurring. Moreover, fluoride treatments are less effective in strengthening periodontal tissue against attack and are not very effective in treating denture materials.

Chlorhexidine gluconate and similar materials such as hexitidine are known to adhere to oral tissues and inhibit plaque formation. These compounds may also adhere to acrylic materials. But these compounds have poor organoleptic qualtities and can produce significant staining on teeth.

Others have tried to coat teeth or dentures using various materials to prevent plaque formation. None of these materials, however, has proven fully effective for dentures. In the case of dentures, the easiest "coating" technique, of course, would be constructing the dentures out of materials that are resistant to plaque attachment. Other techniques have also been tried.

For example, in U.S. Pat. No. 3,120,460 to Tamas, a dentifrice containing an organic titanate such as triethanolamine titanate is used to prevent tartar formation on pyorrhetic teeth.

U.S. Pat. No. 4,150,48 to Lee et al. discloses a liquid paint-on tooth restorative composition. The material comprises barium borosilicate glass and a curable liquid acrylate which hardens on the tooth surface.

U.S. Pat. No. 4,304,766 to Chang discloses a membrane forming dentifrice for application to fluoride-treated teeth. The composition bonds and adheres to the enamel thereby preventing the fluoride from being eluted or washed off the surface of the tooth.

U.S. Pat. No. 4,370,136 to Widman et al. discloses compositions for the treatment of periodontal disease consisting of coating the root surfaces of the periodontally-involved teeth with a film comprising a polycarbonate resin and a methylene chloride solvent.

U.S. Pat. No. 5,139,768 to Friedman discloses an oral composition for the prevention of dental hypersensitivity using strontium salts or potassium, sodium and lithium nitrate embedded in a cellulosic or hydrophobic acrylic polymer forming a varnish that releases the antihypersensitive agent in a long term manner.

U.S. Pat. No. 5,266,305 to Wood et al. discloses the use of copolymers of polyamino acids for the prevention of tartar deposit formation on natural teeth and dentures. The copolymers are formed by the reaction of polysuccinimide with alkyl, alkenyl or aromatic amines and/or alkyl and alkenyl polyamines. The copolymers are incorporated into a toothpaste, gel or mouthwash carrier.

U.S. Pat. No. 5,296,513 to Ige et al. discloses compositions and methods for the preparation of dental polymer shaped articles such as dentures that are resistant to plaque formation. The composition comprises a monomer with at least one (meth)acryloyloxy group, a polyfunctional monomer with two or more (meth)acryloyloxy groups and a monofunctional monomer.

U.S. Pat. No. 5,427,770 to Viccaro et al. teaches toothpaste, gel and mouth wash compositions that include aminoalkyl silicones. Upon use, the silicones bond to the tooth to form a hydrophobic film.

U.S. Statutory Invention Registration No. H83 discloses a number of dental anti-plaque agents comprising certain [ureylenebis (phenylene sulfonylimino)] bis [hydroxynaphthalene sulfonic acids] and derivatives. These compounds inhibit connective tissue destruction and deposition of dental plaque and tartar.

The references discussed above all look to coating the teeth through dentifrice or mouth rinse topical application using various agents. Those references that do mention dentures tend to focus on the base material used in the manufacture of the denture. Like teeth, however, dentures are subject to wear, and a plaque-resistant material may not continue to be resistant over time. Moreover, the plaque-resistant materials available for denture construction are not always the best materials for other design objectives.

What remains missing in the art is an acceptable coating material that can be used with full or partial dentures or dental work to provide a plaque resistant coating for dentures and permanent dental work. Such a coating should be able to be reapplied regularly, during normal cleaning, and should offer superior resistance to plaque formation.

SUMMARY OF THE INVENTION

It is an object of the invention to provide a coating for full or partial dentures or dental work that can be applied using conventional cleaning techniques and that provides good protection against plaque formation.

It is another object of the invention to provide a method for coating full or partial dentures or dental work that provides good resistance to plaque formation.

The objects of the invention are accomplished by providing a cleaning material for full or partial dentures or dental work comprising a copolymer that coats and adheres to the surface of denture material during ordinary cleaning.

It is an advantage of the invention that the copolymer may be used with ordinary cleaning agents found in denture cleansers, dentifrices and other tooth or denture cleaning systems.

Additional objects and advantages of the invention will be apparent from a review of the following detailed description of the invention.

BRIEF DESCRIPTION OF THE DRAWINGS

FIG. 1 is a graph showing the effect of various compositions on plaque growth.

DETAILED DESCRIPTION OF THE INVENTION

The invention broadly may be defined as the provision of a material that coats denture surfaces to reduce formation of plaque on denture surfaces. Unlike a permanent coating, the coating of the invention wears off at least in part during the course of regular use, so it can be reapplied at the next daily cleaning. The wearing away of the coating is advantageous because it allows for exposure of the teeth and denture material to normal cleaning materials.

The coating material may preferably be placed in a denture cleansing formulation, either in a paste or cream or in a denture cleanser tablet. The coating material may be placed in a dentifrice paste, powder or gel or mouthwash or mouth rinse to treat permanent dental work that remains in the mouth along with natural teeth. In addition to the coating material, formulations for cleaning teeth may also comprise antibacterial agents such as Triclosan, anticalculus agents, such as pyrophosphate salts, fluorides, such as sodium fluoride and sodium monofluorophosphate, desensitizing agents like potassium nitrate, potassium chloride, certain strontium salts, tubule blocking agents, preservatives, whitening agents and other known mouthwash or dentifrice ingredients.

While a number of film forming materials are useful as a coating in the invention, the most preferred are polymeric materials for their relative ease of handling. Preferred polymers include polyoxyethylene oxide polymers and copolymers. Especially preferred are polyoxyethylene oxide/vinyl acetate copolymers, and most preferred are polyoxyethylene oxide/vinyl acetate graft copolymers. Of these highly preferred graft copolymers, a series of graft copolymers commercially sold as Sokalan-HP® polymers (BASF Chemical Company, Mount Olive, N.J.), have the best performance characteristics on acrylic denture materials. Especially preferred is one graft copolymer, sold as Sokalan-HP-22. The Sokalan graft copolymers have a molecular weight of about 24,000 and comprise about one part by weight polyethylene oxide to about three parts by weight vinyl acetate.

This superior performance is unexpected since polymeric materials are not generally known for their ability to adhere to denture or tooth surfaces. Such films generally require extra adhesion steps, such as UV-activated photo-curing for methacrylates (See U.S. Pat. No 5,133,957 to Suh et al.) or dissolution in an organic solvent followed by and painting on a tooth surface (See U.S. Pat. No. 3,770,473 to Lepere). Some adherence techniques even require the absence of water, a difficult condition to obtain in the oral cavity.

The film forming material may be incorporated into a cream or paste that is brushed on to a denture material or a dentifrice for use in the mouth. Preferably the film forming material comprises from about 3% to about 40% by weight of the dentifrice, cream or paste. More preferably, the film forming material comprises from about 5% to about 35% of the dentifrice, cream or paste, and most preferably from about 10% to about 20% of the cream or paste.

For treating dentures, the film forming material is preferably incorporated into a denture cleanser in tablet or other solid form designed to work with water as a soaking agent. More preferably, the denture cleanser comprises an effervescent tablet used to clean dentures by soaking for a period of time.

The solid denture cleanser material may incorporate conventional ingredients such as bleaching agents, enzymes, effervescent systems, tableting aids, stabilizers, surfactants and other active and inactive ingredients known to those skilled in the art.

The film forming material may comprise from about 0.5% to about 10% by weight of the tablet. Preferably the material comprises from about 1.0% to about 7% by weight of the tablet, and most preferably, the material comprises from about 3% to about 6% by weight of the tablet.

Other delivery systems may also be used. If the film forming material is incorporated into a mouth wash or rinse, for example, the film forming material may comprise from about 3% to about 10% by weight of the mouth wash or rinse, and preferably about 5% by weight of the composition. Conventional mouth wash or mouth rinse ingredients may also be added.

The invention will be better understood by referring to the following non-limiting examples.

EXAMPLE 1

A dental paste for the application of the protective polymer film and the simultaneous cleaning of dentures or teeth was prepared by mixing the following ingredients. The water soluble ingredients such as the saccharin, color, the humectant and the Sokalan copolymer are mixed first. The abrasives are then dispersed in the water soluble ingredients. The carboxymethylcellulose is dispersed into part of the humectant before addition into the batch to prevent lumps. The flavor, preservatives and sodium lauryl sulfate are added last to obtain a toothpaste slurry. The system is then mixed under vacuum using known equipment such as a Tekmar mill, Ross mixer, or Nauta mixer.

| Ingredient | Function | Wt. % |
|---|---|---|
| Purified water | Solvent | 4.179 |
| Polyoxyethylene oxide/vinyl acetate copolymer (Sokalan HP22) | Film Forming Material | 25 |
| Sodium saccharin | Sweetener | 0.1 |
| Color | Colorant | 0.002 |
| Propylene glycol | Humectant | 25 |
| Glycerin | Humectant | 10 |
| Calcium Carbonate, Silica, Dicalcium Phosphate | Polishing Agents | 25 |
| Sodium carboxymethyl cellulose | Thickener | 1.5 |
| Sodiuxn Lauryl Sulfate | Detergent | 3 |

-continued

| Ingredient | Function | Wt. % |
|---|---|---|
| Flavor | Flavor | 1 |
| Preservative | Preservative | 0.1 |

EXAMPLE 2

An in-vitro study was carried out to determine the ability of Sokalan HP22 to inhibit plaque growth in a toothpaste.

Acrylic slides were brushed with a toothpaste containing either the toothpaste of Example 1 or a placebo not containing the Sokalan HP22. Unbrushed acrylic slides were used as a negative control. The slides were placed in Trypticase soy broth and incubated overnight for plaque growth. Plaque was disclosed with a 0.03% solution of Fuchsin dye. The dye was extracted and spectrophotometer readings were obtained. Percent plaque inhibition was computed and a summary of the results is set out below.

| Trial No. | Toothpaste with polymer | Placebo | Control |
|---|---|---|---|
| 1 | 0.391 | 0.71 | 0.794 |
| 2 | 0.428 | 0.718 | 0.737 |
| 3 | 0.472 | 0.573 | 0.716 |
| 4 | 0.492 | 0.679 | 0.7 |
| 5 | 0.373 | 0.732 | 0.718 |
| 6 | 0.366 | 0.748 | 0.733 |
| 7 | 0.534 | 0.692 | 0.746 |
| 8 | 0.545 | 0.566 | 0.687 |
| 9 | 0.38 | 0.636 | 0.742 |
| 10 | 0.31 | 0.66 | 0.705 |
| mean | 0.429 | 0.671 | 0.728 |
| S.D. | 0.078 | 0.063 | 0.03 |
| % Plaque Inhibition | −41.1% | −7.83% | N/A |
| S.E.M. | 3.2 | 8.3 | N/A |

EXAMPLE 3

A gel toothpaste was prepared using the method set forth in Example 1. The gel was translucent, but could be modified to be transparent using techniques well known in the art such as modifying the relative amounts of water, glycerin and sorbitol. The gel formulation is as follows:

| Ingredient | Wt. % |
|---|---|
| Saccharin | 0.25 |
| Polyethylene oxide/vinyl acetate copolymer (Sokalan HP 22) | 5 |
| Sorbitol | 45 |
| Glycerin | 25 |
| Hydroxyethylcellulose | 1.5 |
| Abrasives (silica) | 15 |
| Sodium Lauryl Sulfate | 2.5 |
| Color | 0.003 |
| Flavor | 1.2 |
| Water | 5 |

EXAMPLE 4

An effervescent denture cleanser tablet for the anti-plaque protection of dentures through an aqueous soak was prepared by mixing the following ingredients and forming a compressed tablet from the mixture:

Denture Cleanser Tablet

| Ingredient | Function | Weight % |
|---|---|---|
| Polyoxyethylene oxide/vinyl acetate copolymer (Sokalan HP22) | Film forming material | 1 |
| Sodium bicarbonate No. 1 USP | Effervescent System | 26.061 |
| Sodium Hexametaphosphate, FCC | Granulating Aid/Anti-tartar agent | 4.606 |
| Polyvinylpyrrolidone (PVP K-30) | Binder | 0.869 |
| Soda Ash, Anhydrous Light | Moisture Absorber | 8.1 |
| Fluorochemical Surfactant (Fluorad FC-129) | Surface Tension Reducer | 0.05 |
| Peppermint Oil | Flavorant | 0.8 |
| Potassium monopersulfate (Oxone) | Oxidizing Agent | 25 |
| Sodium perborate monohydrate | Oxidizing Agent | 5 |
| Sodium Lauryl Sulfoacetate (Lanthanol LAL) | Surfactant | 4 |
| Sodium Stearate, NF | Foam stabilizing agent | 0.5 |
| Citric Acid, Milled, granular | Effervescent system | 18.17 |
| Sodium Benzoate, NF | Tableting aid | 2.875 |
| Polyethylene glycol 8000, NF (Carbowax 8000) | Tableting aid | 2.875 |
| FD&C Blue No. 2 | Colorant | 0.04245 |
| FD&C Yellow No. 5 | Colorant | 0.05155 |

EXAMPLE 5

A mouthwash formulation of the invention comprising the anti-plaque film barrier of the invention was prepared by mixing the following ingredients. The order of adding the ingredients is not critical.

| Ingredient | Weight % |
|---|---|
| Polyethylene oxide vinyl acetate copolymer (Sokalan HP22) | 5 |
| Denatured Alcohol | 7 |
| Sorbitol Solution | 15 |
| Poloxamer 407 | 1 |
| Color | 0.01 |
| Disodium Phosphate | 0.15 |
| Citric Acid | 0.07 |
| Water | q.s. |

EXAMPLE 6

The efficacy of Sokalan HP-22 was directly shown by dipping acrylic slides in a 20% polyethylene oxide/vinyl acetate copolymer solution (Sokalan HP-22) and allowed to dry. Plaque coatings were allowed to grow on the treated slides utilizing commonly employed laboratory techniques to form plaque coated slides. The extent of plaque growth was then compared to control slides not treated with Sokalan HP-22 by staining with Fuchsin dye. Less plaque growth was observed on the treated slides. When the slides were subsequently treated with commercially available effervescent tablets, more plaque was removed from the treated slides than from the control (measured as a percentage of the amount of plaque originally present.

EXAMPLE 7

Denture cleanser tablets containing 1% polyoxyethylene oxide/vinyl acetate copolymer (a 20% active solution) were prepared from the effervescent tablet formulations of Example 4.

The tablets incorporating the copolymer were then used to treat clean acrylic slides by soaking the slides in a solution of the tablets. In this experiment, seven hour soaks were used with fresh tablets employed after each soaking period. The slides were soaked for a total of forty-nine hours.

The amount of plaque grown on the soaked slides was compared to the amount present on an untreated group of slides and was determined spectrophotometrically. In this experiment only 32% of the total plaque growth of an untreated group of slides was found to be present on the slides treated with the copolymer film. Slides treated for forty-nine hours with tablets formulated without the polymer barrier showed a reduction of only 3.2%. The results are shown in FIG. 1 along with other comparative examples using Zonyl FSA, a fluorosurfactant, and Sokalan 9976.

EXAMPLE 8

An in-vivo comparison of denture cleanser tablets containing Sokalan and not containing Sokalan was carried out in an overnight soak test to confirm that the benefits predicted for coated dentures are proven out in actual human use. Denture cleansers were prepared using a commercial tablet and a commercial tablet modified by the addition of Sokalan HP-22. Denture wearers were given samples to use for five consecutive nights of overnight soaking with the assigned tablet followed by two or three days of use without cleaning. A panel of judges then evaluated the amount and coverage of plaque on stained dentures. The degree of staining was rated on a scale of 0 (low)–6 (high), and the coverage percent was rated on a scale from 0–100%

| Comparison of Sokalan/non-Sokalan Denture Cleansers in Vivo | | | | | | |
|---|---|---|---|---|---|---|
| | Stain Mean | Stain SD | p-value | Cvrge mean | Cvrge SD | p-value |
| 2-day plaque growth | | | | | | |
| Tablet w/o Sokalan | 2.59 | 0.73 | 0.22 | 43.2 | 18 | 0.14 |
| Tablet w/ Sokalan | 2.42 | 0.83 | | 37.9 | 14.2 | |
| 3-day plaque growth | | | | | | |
| Tablet w/o Sokalan | 2.26 | 0.7 | 0.13 | 37.3 | 20.9 | 0.03 |
| Tablet w/ Sokalan | 2.07 | 0.63 | | 29.3 | 13.1 | |

There was less plaque buildup with Sokalan treated dentures, and the results were even more pronounced after three days than after two days.

The foregoing description of the invention is intended to illustrate various advantages of the invention and is not intended to limit the scope of the invention in any manner.

What is claimed is:

1. An anti-plaque denture cleanser tablet composition for the cleaning of full or partial dentures comprising a film-forming material consisting of a graft copolymer of polyoxyethylene oxide and vinyl acetate, an effervescent system, oxidizing agents, surfactants and mixtures thereof.

2. The effervescent tablet of claim 1 wherein said effervescent system comprises a mixture of sodium bicarbonate and citric acid.

3. The effervescent tablet composition of claim 2 further comprising granulation aids, tabletting aids, binders, enzymes, anti-tartar agents, colorants, moisture absorbers, flavorants, foam stabilizers and mixtures thereof.

4. The effervescent tablet composition of claim 3 wherein said graft copolymer comprises from about 0.5% to about 20% by weight of the denture cleanser tablet composition.

5. The effervescent tablet composition of claim 4 wherein said graft copolymer comprises from about 0.5% to about 10% by weight of the denture cleanser tablet composition.

6. The effervescent tablet composition of claim 5 wherein said graft copolymer comprises from about 0.5% to 5.0% by weight of the denture tablet compositions.

7. The effervescent tablet composition of claim 6 wherein said oxidizing agents are selected from the group consisting of potassium monopersulfate, sodium perborate monohydrate and mixtures thereof.

8. The effervescent tablet composition of claim 7 that is compressed to a solid tablet form.

9. A method for the prevention of plaque on full or partial dentures comprising the soaking of said full or partial dentures in an effervescent aqueous solution comprising water and an effervescent denture cleanser consisting of a graft copolymer of polyoxyethylene oxide and vinyl acetate, an effervescent system, oxidizing agents, surfactants and mixtures thereof.

10. The method of claim 9 wherein said effervescent system comprises a mixture of sodium bicarbonate and citric acid.

11. The method of claim 10 further comprising granulation aids, tabletting aids, binders, enzymes, anti-tartar agents, colorants, moisture absorbers, flavorants, foam stabilizers and mixtures thereof.

12. The method of claim 11 wherein said graft copolymer comprises from about 0.5% to about 20% by weight of the denture cleanser tablet.

13. The method of claim 12 wherein said graft copolymer comprises from about 0.5% to about 10% by weight of the denture cleanser tablet.

14. The method of claim 13 wherein said graft copolymer comprises from about 0.5% to 5.0% by weight of the denture tablet.

15. The method of claim 14 wherein said oxidizing agents are selected from the group consisting of potassium monopersulfate, sodium perborate monohydrate and mixture thereof.

* * * * *